(12) United States Patent
Hutchings et al.

(10) Patent No.: US 10,968,148 B2
(45) Date of Patent: Apr. 6, 2021

(54) METHOD OF PRODUCING COMPOUND COMPRISING ALKENYL GROUP

(71) Applicant: University College Cardiff Consultants Limited, Cardiff South Glamorgan (GB)

(72) Inventors: Graham John Hutchings, Yorkshire (GB); Stanislaw Edmund Golunski, Oxfordshire (GB); Ewa Nowicka, Cardiff South Glamorgan (GB)

(73) Assignee: UNIVERSITY COLLEGE CARDIFF CONSULTANTS LIMITED, Cardiff South Glamorgan (GB)

( * ) Notice: Subject to any disclaimer, the term of this patent is extended or adjusted under 35 U.S.C. 154(b) by 0 days.

(21) Appl. No.: 15/755,157

(22) PCT Filed: Aug. 11, 2016

(86) PCT No.: PCT/GB2016/052495
§ 371 (c)(1),
(2) Date: Feb. 26, 2018

(87) PCT Pub. No.: WO2017/037416
PCT Pub. Date: Mar. 9, 2017

(65) Prior Publication Data
US 2018/0222820 A1    Aug. 9, 2018

(30) Foreign Application Priority Data

Aug. 28, 2015 (GB) .......... 1515393

(51) Int. Cl.
*C07C 5/42* (2006.01)
*C07C 5/48* (2006.01)
(Continued)

(52) U.S. Cl.
CPC .......... *C07C 5/42* (2013.01); *B01J 23/63* (2013.01); *B01J 35/002* (2013.01);
(Continued)

(58) Field of Classification Search
CPC .... C07C 5/42; C07C 5/48; B01J 23/63; B01J 35/10
See application file for complete search history.

(56) References Cited

U.S. PATENT DOCUMENTS 4,717,779 A * 1/1988 Bricker ............. C07C 5/3332
585/319
6,846,773 B1 * 1/2005 Yokoyama ......... B01J 23/626
502/339
(Continued)

FOREIGN PATENT DOCUMENTS

EP    1533029    5/2005
EP    1916230    4/2008
(Continued)

OTHER PUBLICATIONS

International Search Report dated Jun. 8, 2016 issued for corresponding GB Patent Application No. GB1515393.5.
(Continued)

*Primary Examiner* — Youngsul Jeong
(74) *Attorney, Agent, or Firm* — Jackson Walker LLP (57) ABSTRACT

A method of producing at least one compound comprising an alkenyl group from at least one compound comprising an alkyl group having two or more carbon atoms, the method comprising: (i) Providing a mixture comprising carbon dioxide and at least one compound comprising an alkyl group having two or more carbon atoms; and (ii) Contacting said mixture with a catalyst comprising one or both of palladium and platinum and one or more lanthanide, thereby converting at least a portion of the at least one compound
(Continued)

comprising an alkyl group having two or more carbon atoms into a compound comprising an alkenyl group, the total of the weight of the palladium and/or platinum being more than 0.1 wt % of the catalyst.

21 Claims, 2 Drawing Sheets (51) Int. Cl.
  *B01J 23/63* (2006.01)
  *B01J 35/10* (2006.01)
  *B01J 35/00* (2006.01)
(52) U.S. Cl.
  CPC ............. *B01J 35/1014* (2013.01); *C07C 5/48* (2013.01); *C07C 2521/02* (2013.01); *C07C 2523/10* (2013.01); *C07C 2523/44* (2013.01); *C07C 2523/63* (2013.01); *Y02P 20/52* (2015.11)

(56) References Cited

U.S. PATENT DOCUMENTS

| | | |
|---|---|---|
| 2003/0191020 A1 | 10/2003 | Bharadwaj et al. |
| 2005/0131255 A1 | 6/2005 | Benderly et al. |
| 2007/0260101 A1 | 11/2007 | Carrera et al. |
| 2008/0177117 A1 | 7/2008 | Benderly et al. |
| 2009/0182186 A1* | 7/2009 | Benderly ............. B01J 21/08 585/654 |
| 2011/0213189 A1 | 9/2011 | Mishima et al. |

FOREIGN PATENT DOCUMENTS

| | | | |
|---|---|---|---|
| EP | 2080747 | 7/2009 | |
| EP | 2353712 | 8/2011 | |
| WO | 2004/033089 | 4/2004 | |
| WO | WO-2004033089 A2 * | 4/2004 | ............. B01J 23/10 |

OTHER PUBLICATIONS

International Search Report dated Oct. 20, 2016, issued for corresponding International Application No. PCT/GB2016/052495 from which the present US application is derived.

Demoulin, O., et al., "The Oxidizing Role of CO2 at Mild Temperature on Ceria-Based Catalysts", Applied Catalysis B: Environmental 70 (2007), pp. 284-293.

Carrero, C.A., et al., "Critical Literature Review of the Kinetics for the Oxidative Dehydrogenation of Propane Over Well-Defined Supported Vanadium Oxide Catalysts", ACS Catal., 2014, 4 (10), pp. 3357-3380, Publication Date (Web): Aug. 15, 2014.

Vu, Bao Khanh, et al., "The Roles of CEyZr1-yO2 in Propane Dehydrogenation: Enhancing Catalytic Stability and Decreasing Coke Combustion Temperature", Applied Catalysis A: General, 443-444, 2012, pp. 59-66.

Ansari, Mohd Bismillah, et al., "Carbon Dioxide Utilization as a Soft Oxidant and Promoter in Catalysis", Energy & Environmental Science, 2012, 5, pp. 9419-9437.

Michorczyk, Piotr, et al., "Dehydrogenation of Propane with CO2—A New Green Process for Propene and Synthesis Gas Production", Polish Journal of Chemical Technology, 14, 4, pp. 77-82.

* cited by examiner

METHOD OF PRODUCING COMPOUND COMPRISING ALKENYL GROUP

BACKGROUND OF THE INVENTION

The present disclosure relates to a method of producing a compound comprising an alkenyl group (such as an alkene, for example a $C_{2-12}$alkene, or an alkenyl aryl or alkenyl heteroaryl compound, for example styrene) and a catalyst used in such a method.

The present invention concerns the production of compounds comprising an alkenyl group. More particularly, but not exclusively, this invention concerns the production of compounds comprising an alkenyl group from compounds comprising alkyl groups. The invention also concerns a catalyst for use in such methods.

The production of alkenes (such as propene) from alkanes (such as propane) is known to those skilled in the art. For example, the alkene may be merely dehydrogenated, producing the alkene and hydrogen. This is a strongly endothermic reaction and it is equilibrium limited, therefore, it has to be performed at a high temperature, which may lead to low selectivity to propene and to coking. This dehydrogenation reaction may be catalysed using a chromia catalyst, a platinum-tin catalyst or a Zn catalyst on a calcium-aluminium support. Due to coke deposition, the catalyst typically needs to be periodically regenerated.

Alternatively, oxygen may be used to facilitate an oxidative dehydrogenation of the alkane to form the alkene and water, typically in the presence of a $V_2O_5$ catalyst. This reaction is strongly exothermic, and there is a significant risk of the alkane oxidising to unwanted products, such as carbon dioxide. There may be significant safety issues associated with this process if operated close to the explosive limits of either the reactants or products.

$CO_2$ has also been used in the oxidative dehydrogenation of alkanes. The reaction temperature at which the process operates is typically 600-650° C., which can lead to coking.

The present invention seeks to mitigate one or more of the above-mentioned problems. Alternatively or additionally, the present invention seeks to provide an improved method of producing alkenes and an improved catalyst for use in such methods.

SUMMARY OF THE INVENTION

In accordance with a first aspect of the present invention, there is provided a method of producing at least one compound comprising an alkenyl group from at least one compound comprising an alkyl group having two or more carbon atoms, the method comprising:
  (i) Providing a mixture comprising carbon dioxide and at least one compound comprising an alkyl group having two or more carbon atoms;
  (ii) Contacting said mixture with a catalyst comprising (a) one or both of palladium and platinum, and (b) one or more lanthanide, thereby converting at least a portion of the at least one compound comprising an alkyl group having two or more carbon atoms into a compound comprising an alkenyl group, the total weight of the palladium and/or platinum being more than 0.1 wt % of the catalyst.

The method of the present invention facilitates the production of compounds comprising an alkenyl group (such as alkenes) using relatively mild reaction conditions. For example, the method of the present invention may not require the presence of steam and/or hydrogen, and therefore step (ii) may take place in the absence of steam, oxygen and/or hydrogen. In this connection, one or more of hydrogen, oxygen and steam are optionally not provided in the mixture. It is preferred that one or both of hydrogen and steam are not provided.

The compound(s) comprising an alkyl group having at least two carbon atoms may be an alkane, such as a $C_2$-$C_{12}$ alkane. The compound(s) comprising an alkyl group having at least two carbon atoms may be an alkyl aryl compound, such as an alkyl benzene, for example ethyl benzene, or a alkenyl heteroaryl compound.

The respective compound(s) comprising an alkyl group having two or more carbon atoms undergo an oxidative dehydrogenation to produce a respective compound comprising an alkenyl group. Therefore, a particular alkane will produce a particular alkene. For example, propane will produce propene, butane will produce butane, pentane will produce pentene, and so on. For example, ethyl benzene will produce styrene, the ethyl group of the ethyl benzene forming an ethenyl group.

Those skilled in the art will appreciate that the mixture is contacted with the catalyst under conditions in which at least a portion of the at least one compound comprising an alkyl group having at least two carbon atoms is converted into at least one compound comprising an alkenyl group. In this connection, step (ii) is typically performed at an elevated temperature, typically at least 300° C., at least 350° C., at least 400° C., at least 450° C., at least 500° C., at least 510° C., at least 520° C. and optionally at least 530° C. Step (ii) is optionally performed at a temperature which is up to 600° C., up to 580° C., up to 570° C., up to 560° C., up to 550° C., up to 540° C., up to 530° C., up to 520° C., up to 510° C. and optionally up to 500° C. Said temperature is optionally from 450 to 600° C., from 470 to 570° C., from 480 to 550° C., from 490 to 540° C., from 490 to 520° C. and optionally from 490 to 510° C. Said temperature is optionally about 500° C. Applicant has discovered that significant fragmentation of the substrate (such as an alkane) may occur at temperatures above 550° C., especially above 600° C.; and that below 450° C., especially below 300° C., activity is relatively poor.

The mixture is typically passed through a stationary catalyst, in which case the mixture is typically provided at a slightly positive pressure so as to cause flow of the mixture over the stationary catalyst. Those skilled in the art will realise that catalyst may not be stationary, for example, if the reaction takes place is a fluidised bed reactor.

Said mixture may comprise more than one alkane (such as a $C_{2-12}$alkane; for example a $C_{2-4}$alkane). Said mixture may comprise more than one alkyl aryl or alkyl heteroaryl (such as a $C_{2-12}$alkyl aryl, for example $C_{2-4}$alkyl aryl). Said mixture may comprise a mixture of alkane (such as a $C_{2-12}$alkane; for example a $C_{2-4}$alkane) and one or more alkyl aryl (such as a $C_{2-12}$alkyl aryl, for example $C_{2-4}$alkyl aryl).

The mixture is typically provided as a gas.

The mixture may comprise at least 5 mol %, at least 10 mol %, at least 15 mol %, at least 20 mol %, at least 25 mol %, at least 30 mol %, at least 35 mol % and optionally at least 40 mol % carbon dioxide. The mixture may comprise up to 60 mol %, up to 50 mol %, up to 40 mol %, up to 35 mol %, up to 30 mol %, up to 25 mol % and optionally up to 20 mol % carbon dioxide. The mixture may comprise from 20-50 mol %, optionally from 25-40 mol % and optionally from 30-40 mol % carbon dioxide.

The mixture may comprise at least 5 mol %, at least 10 mol %, at least 15 mol %, at least 20 mol %, at least 25 mol %, at least 30 mol %, at least 35 mol % and optionally at least 40 mol % of the at least one compound comprising an alkyl group having two or more carbon atoms. The mixture may comprise up to 60 mol %, up to 50 mol %, up to 40 mol %, up to 35 mol %, up to 30 mol %, up to 25 mol % and optionally up to 20 mol % of the at least one alkane or alkyl aryl or alkyl heteroaryl. The mixture may comprise from 20-50 mol %, optionally from 25-40 mol % and optionally from 30-40 mol % of the at least one compound comprising an alkyl group having two or more carbon atoms.

The molar ratio of carbon dioxide to the at least one compound comprising an alkyl group having two or more carbon atoms may be at least 0.1:1, at least 0.2:1, at least 0.3:1, at least 0.5:1, at least 0.6:1, at least 0.7:1, at least 0.8:1, at least 0.9:1, at least 1:1, at least 1.1:1, at least 1.2:1, at least 1.3:1, at least 1.4:1, at least 1.5:1, at least 1.7:1, at least 2:1, at least 3:1, at least 5:1, at least 6:1, at least 7:1, at least 8:1, at least 9:1 and optionally at least 10:1.

The molar ratio of carbon dioxide to the at least one compound comprising an alkyl group having two or more carbon atoms may be up to 10:1, up to 5:1, up to 3:1, up to 2:1, up to 1.6:1, up to 1.5:1, up to 1.4:1, up to 1.3:1, up to 1.2:1, up to 1.1:1, up to 1:1, up to 0.9:1, up to 0.8:1, up to 0.7:1, up to 0.6:1, up to 0.5:1, up to 0.4:1, up to 0.3:1 and optionally up to 0.2:1.

The molar ratio of carbon dioxide to the at least compound comprising an alkyl group having two or more carbon atoms may be from 0.1:1 to 10:1, from 0.2:1 to 5:1, from 0.3:1 to 3:1, from 0.5:1 to 2:1, from 0.5:1 to 1.5:1, from 0.7:1 to 1.3:1, from 0.8:1 to 1.2:1 and from 0.9:1 to 1.1:1 (for example about 1:1). It has been surprisingly found that the reaction proceeds particularly effectively if there is approximately the same amount of carbon dioxide and compound(s) to be dehydrogenated.

As used herein, the term "alkyl" means both straight and branched chain saturated hydrocarbon groups. Examples of alkyl groups include ethyl, n-propyl, iso-propyl, n-butyl, t-butyl, i-butyl, sec-butyl, pentyl and hexyl groups. Among unbranched alkyl groups, there are preferred methyl, ethyl, n-propyl, iso-propyl, n-butyl groups. Among branched alkyl groups, there may be mentioned t-butyl, i-butyl, 1-ethylpropyl and 1-ethylbutyl groups.

As used herein, the term "aryl" means a monocyclic or bicyclic aromatic carbocyclic group. Examples of aryl groups include phenyl and naphthyl. A naphthyl group may be attached through the 1 or the 2 position. In a bicyclic aromatic group, one of the rings may, for example, be partially saturated. Examples of such groups include indanyl and tetrahydronaphthyl. Specifically, the term $C_{5-10}$ aryl is used herein to mean a group comprising from 5 to 10 carbon atoms in a monocyclic or bicyclic aromatic group. A particularly preferred $C_{5-10}$ aryl group is phenyl.

As used herein, the term "heteroaryl" means an aromatic cyclic group of carbon atoms wherein from one to three of the carbon atoms is/are replaced by one or more heteroatoms independently selected from nitrogen, oxygen or sulfur. A heterocyclyl group may, for example, be monocyclic or bicyclic. Preferably the heteroaryl is a $C_{5-10}$-heteraryl. In a bicyclic heterocyclyl group there may be one or more heteroatoms in each ring, or only in one of the rings. A heteroatom is preferably O or N. Heterocyclyl groups containing a suitable nitrogen atom include the corresponding N-oxides. Examples of monocyclic heteroaryl groups include furanyl, thienyl, pyrrolyl, oxazolyl, thiazolyl, imidazolyl, oxadiazolyl, thiadiazolyl, pyridyl, triazolyl, triazinyl, pyridazyl, isothiazolyl, isoxazolyl, pyrazinyl, pyrazolyl and pyrimidinyl. Examples of bicyclic heteroaryl groups include quinoxalinyl, quinazolinyl, pyridopyrazinyl, benzoxazolyl, benzothiophenyl, benzimidazolyl, naphthyridinyl, quinolinyl, benzofuranyl, indolyl, benzothiazolyl, oxazolyl[4,5-b] pyridiyl, pyridopyrimidinyl, isoquinolinyl and benzodroxazole.

The mixture may comprise at least one (and optionally more than one) $C_2$-$C_{12}$ alkane, for example one or more $C_2$alkane, $C_3$alkane, $C_4$alkane, $C_5$alkane, $C_6$alkane, $C_7$alkane, $C_8$alkane, $C_9$alkane, $C_{10}$alkane, $C_{11}$alkane or $C_{12}$alkane. The mixture may comprise at least one (and optionally more than one) $C_2$-$C_6$ alkane. The mixture may comprise at least one (and optionally more than one) $C_2$-$C_4$ alkane. The mixture may comprise at least one (and optionally more than one) $C_2$-$C_{12}$ alkyl $C_{5-10}$aryl, such as alkyl benzene, such as $C_2$-$C_{12}$ alkyl benzene, such as $C_2$-$C_6$ alkyl benzene or $C_2$-$C_4$ alkyl benzene, for example ethyl benzene. The mixture may comprise at least one (and optionally more than one) $C_2$-$C_6$ alkyl $C_{5-10}$aryl. The mixture may comprise at least one (and optionally more than one) $C_2$-$C_4$ alkyl $C_{5-10}$aryl. The mixture may comprise at least one (and optionally more than one) $C_2$-$C_{12}$ alkyl $C_{5-10}$heteroaryl. The mixture may comprise at least one (and optionally more than one) $C_2$-$C_6$ alkyl $C_{5-10}$heteroaryl. The mixture may comprise at least one (and optionally more than one) $C_2$-$C_4$ alkyl $C_{5-10}$heteroaryl The mixture may comprise one or more inert component. "Inert" refers to the component not reacting with any of the reagents or reaction products under the reaction conditions provided. The inert component may comprise nitrogen gas ($N_2$), for example. The mixture may comprise up to 60 mol %, optionally up to 50 mol %, optionally up to 40 mol %, optionally up to 30 mol % of said one or more inert component. The mixture may comprise optionally at least 5 mol %, optionally at least 10 mol % and optionally at least 20 mol % of said one or more inert component.

The method may comprise regenerating the catalyst. The catalyst may optionally be regenerated by contacting the catalyst with an oxidising agent, such as carbon dioxide or oxygen, typically at an elevated temperature. It will be apparent to those skilled in the art that the catalyst may be reused once it has been regenerated. Those skilled in the art will also recognise that the regenerated process may not be totally effective i.e. the catalyst may not be regenerated to its initial, pre-use state.

Those skilled in the art will recognise that contacting the mixture with the catalyst will not result in the reaction of all of the compounds which could be dehydrogenated. The method may therefore comprise contacting at least a portion of the mixture with the catalyst more than once. This is particularly the case if the catalyst is static. This may be provided by providing a reactor feedback loop. Such a reactor feedback loop may comprise a conduit located downstream of the catalyst, the conduit providing a fluid passage to feed fluid to a position upstream of the catalyst. Therefore, the method may comprise passing a treated portion of the mixture from a position downstream of the catalyst to the catalyst, typically by providing the treated portion upstream of the catalyst. "Treated" indicates that the portion of the mixture has contacted the catalyst at least once.

The method of the present invention may be particularly effective, and so may permit relatively high gas hourly space velocities (GHSV) to be used. The GHSV of the mixture may therefore be at least 1000/h, at least 2000/h, at least 3000/h, at least 4000/h, at least 5000/h, at least 6000/h, at least 7000/h, at least 8000/h, at least 9000/h and at least 10,000/h. GHSV is measured at 25° C. and at a pressure of 1 atm.

As indicated above, the catalyst comprises more than 0.1 wt % of palladium and/or platinum (indicating that the total weight of the palladium and platinum [whichever are present in the catalyst] is more than 0.1 wt % of the weight of the catalyst). Those skilled in the art will note that the catalyst need not comprise both platinum and palladium. The catalyst may comprise at least 0.5 mol % palladium and/or platinum, at least 1.0 mol %, at least 1.5 mol %, at least 2.0 mol %, at least 3.0 mol %, at least 4.0 mol %, at least 5.0 mol %, at least 6.0 mol %, at least 7.0 mol %, at least 8.0 mol %, at least 9.0 mol % and at least 10.0 mol % palladium and/or platinum. The catalyst may comprise up to 15.0 mol % palladium and/or platinum, up to 10.0 mol %, up to 8.0 mol %, up to 7.0 mol %, up to 6.0 mol %, up to 5.0 mol %, up to 4.0 mol %, up to 3.0 mol % and up to 2.0 mol % palladium and/or platinum. The catalyst may comprise from 1.0 to 8.0 mol % palladium and/or platinum, from 2.0 to 7.0 mol % and optionally from 3.0 to 6.0 mol % palladium and/or platinum.

The catalyst may comprise at least 1.0 mol % of the one or more lanthanide, at least 2.0 mol %, at least 3.0 mol %, at least 4.0 mol %, at least 5.0 mol %, at least 6.0 mol %, at least 7.0 mol %, at least 8.0 mol %, at least 9.0 mol %, at least 10.0 mol %, at least 12.0 mol % and optionally at least 15.0 mol % of the one or more lanthanide. The catalyst may comprise up to 30.0 mol % of the one or more lanthanide, up to 25.0 mol %, up to 20.0 mol %, up to 15.0 mol %, up to 13.0 mol %, up to 12.0 mol %, up to 10.0 mol %, up to 8.0 mol %, up to 7.0 mol % and up to 5.0 mol % of the one or more lanthanide. The catalyst may comprise from 5.0 to 15.0 mol % of the one or more lanthanide, from 6.0 to 13.0 mol % and optionally from 8.0 to 12.0 mol % of one or more lanthanide.

The molar ratio of the one or more lanthanide series of elements to the one or both of palladium and platinum is optionally from 0.2:1 to 5:1, from 0.3:1 to 4:1, from 0.5:1 to 3:1, from 1:1 to 15:1, optionally from 1:1 to 2.5:1 and optionally from 1.5:1 to 2.5:1.

The one or more lanthanide may be selected from the group consisting of the naturally-occurring lanthanides, and combinations thereof. The one or more lanthanide may be selected from the group consisting of lanthanum, cerium, praseodymium, neodymium, samarium, terbium, and combinations thereof. The one or more lanthanide may be selected from the group consisting of cerium, praseodymium, samarium, terbium, and combinations thereof. The one or more lanthanide may comprise cerium.

Whilst not wishing to be bound by theory, it is understood that the one or more lanthanide is acting as a catalytic moiety, and is not merely providing an unreactive, high surface area support for other catalytic moieties, such as the one or both of palladium and platinum.

The surface area of the catalyst may be from 50 to 300 m²/g, optionally from 60 to 250 m²/g and optionally from 70 to 150 m²/g. The surface area may be determined using BET analysis.

The catalyst may be prepared by any suitable method known to those skilled in the art. For example, the catalyst may be prepared using physical grinding or co-precipitation.

The catalyst may be provided in any suitable form. For example, the catalyst may be provided as particles (such as granules, beads, pills, pellets or powders) of any suitable size, or as a coating (in a plate reactor or in a monolith reactor, for example).

The catalyst may comprise a thermal stabiliser for stabilising one or more lanthanide. The thermal stabiliser may comprise zirconium. Zirconium oxide provides thermal stabilisation for certain oxides of lanthanides, such as ceria, and inhibits the sintering of said oxides. If the catalyst comprises zirconium, then the molar ratio of zirconium to the one or more lanthanide (in particular, cerium) is optionally at least 1:4, 1:3, at least 1:2 and optionally at least 1:1.5. If the catalyst comprises zirconium, then the molar ratio of zirconium to the one or more lanthanide (in particular, cerium) is optionally no more than 3:1, no more than 2:1, no more than 1.5:1, no more than 1.3:1, no more than 1.2:1 and optionally no more than 1:1.

If the catalyst comprises zirconium, then the catalyst may comprise at least 2.0 mol % zirconium, at least 3.0 mol %, at least 4.0 mol %, at least 5.0 mol %, at least 6.0 mol %, at least 7.0 mol %, at least 8.0 mol %, at least 9.0 mol % and optionally at least 10.0 mol % zirconium. If the catalyst comprises zirconium, then the catalyst may comprise up to 20.0 mol % zirconium, up to 15.0 mol %, at least 13.0 mol %, up to 12.0 mol %, up to 11.0 mol %, up to 10.0 mol %, up to 9.0 mol %, up to 8.0 mol % and optionally up to 7.0 mol % zirconium. The catalyst may comprise from 4.0 to 12.0 mol % zirconium and optionally from 5.0 to 10.0 mol %.

Those skilled in the art will realise that the reference herein to a particular metal (e.g. platinum, palladium and lanthanide) does not mean that the metal is provided as an isolated metal i.e. in a zero oxidation state. For example, substantially all of the palladium and platinum in a virgin (unused) sample of catalyst will be in a positive oxidation state; as the catalyst is used, any platinum and palladium will typically be reduced to a zero oxidation state. Similarly, the one or more lanthanide in a virgin sample will typically have a proportion in a lower oxidation state and a proportion in a higher oxidation state; as the catalyst is used, the proportion in the lower oxidation state will increase, and the proportion in the high oxidation state will decrease.

The catalyst may comprise a support and one or more catalytic species adhered to said support. In the present case, the one or both of palladium and platinum is typically adhered to a support. Additionally, one or more lanthanide may be adhered to a support. Alternatively or additionally, one or more lanthanide may be provided by a support; for example, the support may comprise lanthanum, cerium, praseodymium, neodymium, samarium, terbium, and combinations thereof; or the support may comprise; cerium, praseodymium, samarium, terbium, and combinations thereof; or the support may comprise cerium. Therefore, the support may provide catalytic activity. Alternatively, the support may be substantially inert. The support may comprise one or more silicon oxides, one or more titanium oxides or one or more aluminium oxides. The support may comprise one or more zirconium oxide, for example.

If the catalyst comprises aluminium, then catalyst optionally comprises at least 1.0 mol % aluminium, at least 2.0 mol %, at least 3.0 mol %, at least 4.0 mol %, at least 5.0 mol %, at least 6.0 mol %, at least 7.0 mol %, at least 8.0 mol %, at least 9.0 mol %, at least 10.0 mol %, at least 12.0 mol %, optionally at least 15.0 mol % aluminium, and optionally at least 18 mol %. The catalyst may comprise up to 30.0 mol % aluminium, up to 25.0 mol %, up to 20.0 mol %, up to 15.0 mol %, up to 13.0 mol %, up to 12.0 mol %, up to 10.0 mol %, up to 8.0 mol %, up to 7.0 mol % and up to 5.0 mol % aluminium. The catalyst may comprise from 9.0 to 20.0 mol % aluminium, for example.

If the catalyst comprises aluminium, then the molar ratio of aluminium to the one or more lanthanide (in particular, cerium) is optionally at least 1:4, 1:3, at least 1:2, at least 1:1.5, at least 1:1 and optionally at least 1.5:1. If the catalyst comprises aluminium, then the molar ratio of aluminium to the one or more lanthanide (in particular, cerium) is optionally no more than 5:1, no more than 4:1, no more than 3:1, no more than 2:1 and optionally no more than 1:1. Optionally, the molar ratio of aluminium to the one or more lanthanide (in particular, cerium) is from 1:2 to 3:1.

The catalyst may comprise oxygen which may typically be present in the form of oxide ($O^{2-}$) species. The catalyst may comprise at least 10 mol %, at least 20 mol %, at least 30 mol %, at least 40 mol % and optionally at least 50 mol % oxygen. The catalyst may comprise no more than 70 mol %, no more than 60 mol %, no more than 50 mol % and optionally no more than 40 mol % oxygen.

The conversion of at least one compound comprising an alkyl group having at least two carbon atoms may be at least 2%, optionally at least 3%.

The method of the present invention may optionally provide end products substantially devoid of fragmentation products of the compound(s) comprising an alkyl group having at least two carbon atoms.

The mol % content of the various constituents of the catalyst may, for example, be determined merely from the relative amounts of the materials used to make the catalyst.

The one or more lanthanide may optionally be replaced by one or more other metals. Such other metals would typically be reducible metal species, such as iron in an oxidation state of 3, vanadium in an oxidation state of 5, or molybdenum in an oxidation state of 6.

In accordance with a second aspect of the present invention, there is provided a catalyst for use in the method of the first aspect of the present invention. The catalyst may comprise those features described above in relation to the method of the first aspect of the present invention.

In accordance with a third aspect of the present invention, there is provided use of carbon dioxide to perform oxidative dehydrogenation of at least one compound comprising an alkyl group having two or more carbon atoms by contacting the carbon dioxide and the at least one compound comprising an alkyl group with a catalyst comprising (a) palladium and/or platinum, and (b) one or more lanthanide, the total weight of the palladium and/or platinum being more than 0.1 wt % of the catalyst.

The use of the third aspect of the present invention may comprise those features described above in relation to the method of the first aspect of the present invention. In particular, the at least one compound comprising an alkyl group may be at least one alkane or an alky aryl compound, such as ethyl benzene. For example, the carbon dioxide is typically provided in a mixture of gases, said mixture optionally having the properties of the mixture described above in relation to the first aspect of the present invention.

DESCRIPTION OF THE DRAWINGS

Embodiments of the present invention will now be described by way of example only with reference to the accompanying schematic drawings of which.

DETAILED DESCRIPTION

Method of Making Catalysts

Requisite amounts of Ce (acac)$_3$ (and Al(acac)$_3$ and/or Zr(acac)$_4$ if Al and/or Zr are to be incorporated into the catalyst) were added together and ground thoroughly for period of 10 mins using mortar and pestle to form a homogenous powder. The powder was heat treated in flowing air at 300° C. for 2 h, heating rate 5° C./min. Once the powder had been calcined, it was ground again for 30 sec. This process provided the support comprising Ce (and optionally Al and Zr).

Pd was wet impregnated onto the calcined support as will now be described. Requisite amount of support was added to an aqueous solution of a Pd-containing precursor (Pd (NH$_3$)$_4$ (NO$_3$)$_2$ (10% wt in H$_2$O, Sigma Aldrich), under vigorous stirring at room temperature. A few drops of HPLC water were added to this mixture to enable better mixing of powder with Pd solution. The solution was agitated in this way until it formed a paste, which was dried at room temperature overnight and further ground again using mortar and pestle for minimum 1 min to obtain homogeneous powder. Catalyst was further calcined using following conditions: flowing air, T=500° C., heating rate 10° C./min, t=4 hrs.

Catalyst 1

Catalyst 1 comprised palladium loaded at 5 mol % onto a CeO$_2$ support, and was made using the general method described above.

Catalyst 2

Catalyst 2 comprised 5% Pd/CeZrAl$_2$O$_7$, and was made using the general method described above. The elemental composition of Catalyst 2 was investigated using transmission electron microscope energy dispersive x-ray spectroscopy (TEM EDX), and was determined to be 68.0% O, 10.3% Al, 6.9% Zr, 5.2% Pd and 9.6% Ce. The values determined by EDX were reasonably consistent with the values determined by the amounts of starting material used. The catalyst was determined to have a surface area of 82 m$^2$/g by BET analysis. This compares with 100 m$^2$/g for CeZrO$_x$ and 104 m$^2$/g for CeZrAlO$_x$.

X-ray photelectron spectroscopy (XPS) analysis of Catalyst 2 indicated that the Pd(0) content of the surface palladium was initially 0%, with a Pd$^{2+}$ content of 100%, and that the Ce$^{3+}$ content was 27% of the Ce, with a Ce$^{4+}$ content of 73%. After use of the catalyst, XPS indicated that the Pd(0) content of the surface palladium was 100%, with a Pd$^{2+}$ content of 0%, and that the Ce$^{3+}$ content was 37% of the Ce, with a Ce$^{4+}$ content of 63%. X-ray absorption near edge structure spectroscopy (XANES) indicates that the particle size in the used catalyst is greater than that of the virgin, unused catalyst.

The catalysts mentioned above were used in exemplary embodiments of the method of the present invention, as will now be described by way of example only.

General Method

Catalytic measurements were performed using a fixed bed laboratory micro reactor at atmospheric pressure, keeping GHSV at 6000 h$^{-1}$ and total flow rate of 15 mL min$^{-1}$. Catalyst (0.2 g) was loaded into a stainless steel reactor tube (length 30 cm, diameter 1.2 cm) and placed between 2 quartz wool portions. Before commencing the reaction, catalyst was pre-treated inside the reactor tube in the flow of helium (10 ml/min) at temperature of 110° C. for period of 30 mins to remove any impurities. The catalyst was then heated to the desired temperature and the catalyst was exposed to the reaction mixture. The reaction mixture comprised He, $CO_2$ and $C_3H_8$, with 26% He, and the rest being $CO_2$ and $C_3H_8$. The reactants and products were analysed by a Varian 3800 online gas chromatograph using Porapak Q and Molsieve columns with TCD and FID detectors.

Example 1

The method as generally described above was performed with Catalyst 1. Catalyst 1 was placed in the microreactor which was then heated to 500° C. The reaction mixture comprised a 9:1 mixture of carbon dioxide:propane. The GHSV was 6385.7/h. After 30 min of reaction, the conversion % of carbon dioxide was about 16% and the conversion % of propane was about 33%.

Example 2

The method of Example 1 was repeated using Catalyst 2 instead of Catalyst 1. The conversion % of carbon dioxide was about 17% and the conversion % of propane was about 34%.

Comparative Example 1

The method of Example 1 was repeated using $CeO_2$ catalyst instead of Catalyst 1. The conversion % of carbon dioxide was about 3.5% and the conversion % of propane was about 5%.

The data of Examples 1, 2 and Comparative Example 1 indicate that the presence of palladium is advantageous. Furthermore, Catalyst 2 was found to be more stable than Catalyst 1, being attributable to the $ZrO_2$ in Catalyst 2 providing a thermal stabiliser for $CeO_2$ to inhibit sintering of $CeO_2$.

Further Examples

Figure 1:
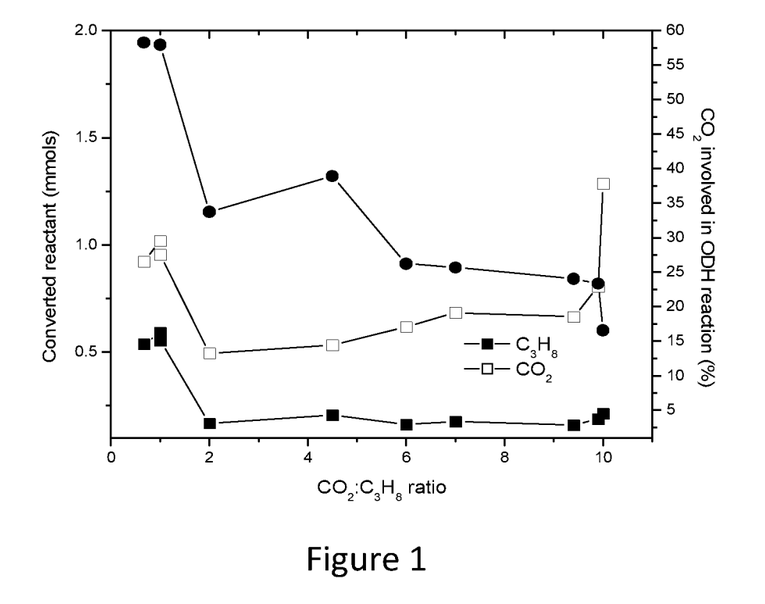
FIG. 1 shows how the conversion % of carbon dioxide and propane, and the amount of carbon dioxide involved in the reaction varies with the relative amounts of carbon dioxide and propane in an embodiment of the method of the present invention.

The effect of the ratio of carbon dioxide:propane on the respective conversion % of carbon dioxide and propane was investigated using Catalyst 2 using the method of Example 2, with a variation in the ratio of carbon dioxide:propane. The results are shown in FIG. 1, with filled squares denoting the conversion of propane, open squares denoting the conversion of carbon dioxide and filled circles denoting the percentage of the carbon dioxide involved in the oxidative dehydrogenation reaction. FIG. 1 indicates that for Catalyst 2, a molar ratio of 1:1 for the carbon dioxide:propane resulted in the highest conversion of both the oxidant and the substrate.

Effect of Catalyst Temperature

Applicant investigated how catalyst temperature affected the reaction in relation to Catalyst 2 by varying the catalyst temperature between 400 and 600° C. It was found that at temperatures lower than 500° C., the activity of the catalyst is relatively poor, whereas temperatures higher than 550° C. the fragmentation of propane is significant. A temperature of about 500° C. proved to be effective because it facilitates the formation of propene, but reduces the risk of coking, and of the fragmentation of propane. Furthermore, use of this temperature reduces the risk of damaging the $CeO_2$ catalyst compared to higher temperatures.

Figure 2:
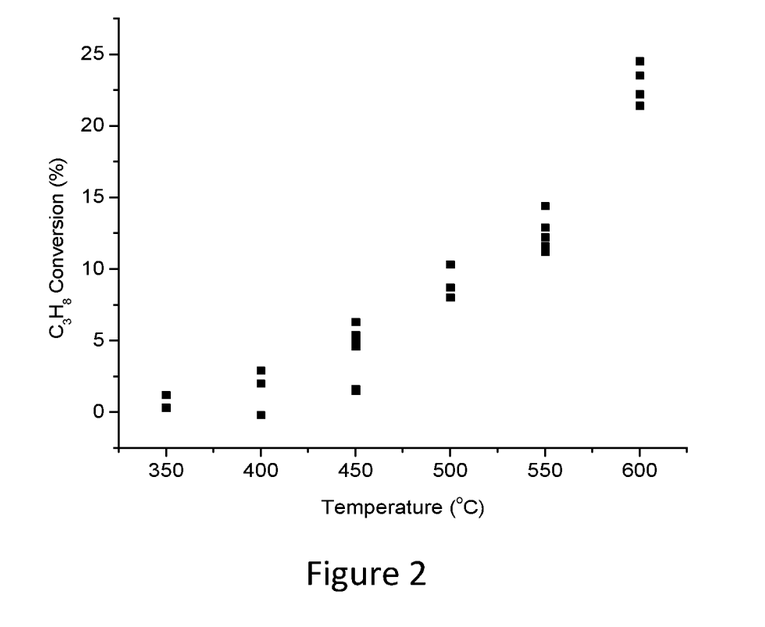
FIG. 2 shows how the conversion % of propane varies with temperature in a in a further example of an embodiment of the present invention.
Figure 3:
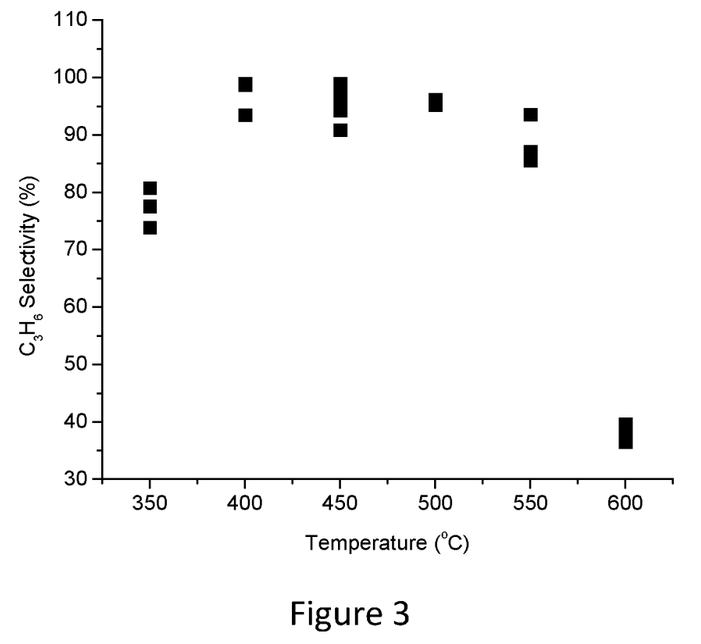
FIG. 3 shows how the selectivity % for propene varies with temperature in a further example of an embodiment of the present invention.

The effect of catalyst temperature was further studied by examining % conversion of propane and % selectivity for propene as a function of temperature using the General Method set-out above. The conditions were: Catalyst 2, total flow rate—15 ml/min, 26% He, 37% $CO_2$, 37% propane, GHSV—6000 h$^{-1}$. The results are shown in FIGS. 2 and 3. The results show that as the temperature increases, the % conversion of propane increases, but that selectivity for propene drops-off significantly at temperatures above 550° C.

Effect of GHSV

Figure 4:
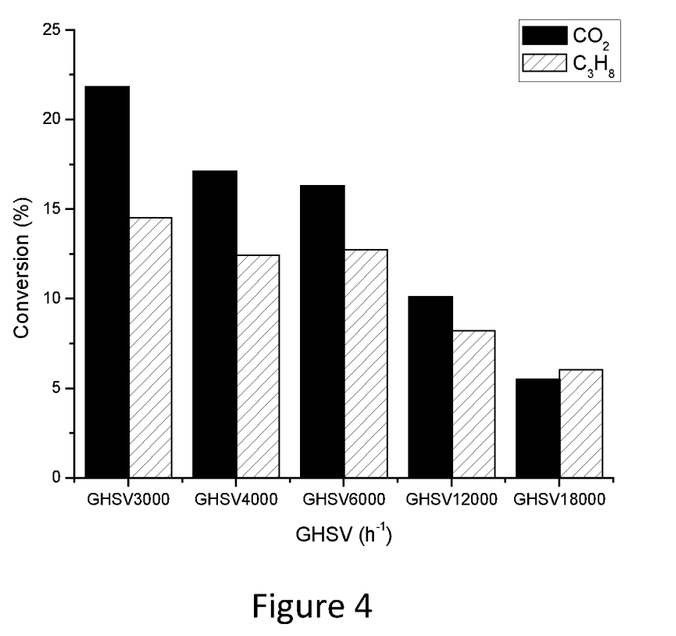
FIG. 4 shows how the conversion of carbon dioxide and propane varies with the GHSV in a further example of an embodiment of the present invention.

The effect of GHSV on % conversion for both carbon dioxide and propane was studied using Catalyst 2 and the General Method described above, with the catalyst maintained at 500° C. The conditions were: 26% He, 37% $CO_2$, 37% propane. The results are shown in FIG. 4. FIG. 4 indicates that for Catalyst 2, the % conversion for both carbon dioxide and propane decreases as GHSV increases over the range of GHSV studied.

Deactivation and Regeneration of Catalyst 2

Catalyst 2 is observed to deactivate over time when exposed to the mixture comprising carbon dioxide and propane. The conversion % of propane is seen to drop over time to a "steady state" value of about 4%. This deactivation is associated with the reduction of the catalyst. Without wishing to be found by theory, it is believed that palladium may be reduced from a +2 oxidation state to a 0 oxidation state, and an increased proportion of the cerium is at a lower oxidation state. It was observed that the catalyst could be regenerated by exposing the catalyst to an oxidant at elevated temperature (e.g. 6 mL/min. flow of carbon dioxide at 500° C. for about 2 hours). It was found that Catalyst 2 could be regenerated twice using carbon dioxide. It was also observed that Catalyst 2 could be regenerated using oxygen gas. It was also observed that heating the catalyst to 500° C. in an inert atmosphere did not lead to any significant regeneration of the catalyst.

Proposed Reaction Scheme

Without wishing to be bound by theory, applicant believes that carbon dioxide is disassociating on the catalyst to form carbon monoxide and an oxygen species. The oxygen species reacts with the propane to form propene and water. The hypothesis that carbon dioxide is forming carbon monoxide is supported by observations made when catalysts are exposed to pulses of carbon dioxide. In this connection, when virgin Catalyst 2 at 455° C. is exposed to pulses of carbon dioxide, then carbon monoxide is produced (as detected by mass spectrometry using Temporal Analysis of Product (TAP)). When used Catalyst 2 at 455° C. is exposed to carbon dioxide, then carbon dioxide is still produced, but in smaller quantities. These effects were observed not only in relation to Catalyst 2, but also in relation to Pd/CeZrAl.

Applicant has demonstrated that it is possible to perform oxidative dehydrogenation of alkanes using carbon dioxide at a relatively low temperature by using a catalyst comprising palladium and/or platinum at more than a trace level (i.e. more than 0.1 wt %) and one or more lanthanide (for example cerium).

The examples above illustrate the use of the catalysts to facilitate oxidative dehydrogenation of propane. Those skilled in the art will realise that other substrates may be treated using the same catalysts, such as any alkane, in particular $C_2$-$C_{12}$ alkanes. Furthermore, other species comprising alkyl groups comprising at least 2 carbon atoms may be treated, for example, ethyl benzene to form styrene.

The examples above demonstrate the use of 5 mol % palladium. Those skilled in the art will realise that different loadings of palladium/platinum may be used.

The examples above illustrate the passage of a gas over a static catalyst. Those skilled in the art will realise that other arrangements may be used, for example, a fluidised bed arrangement.

The examples above disclose the use of an inert gas. An inert gas need not be used. Furthermore, if an inert gas is used, an alternative gas to helium may be used, such as nitrogen.

The examples above illustrate the use of palladium in conjunction with cerium. Platinum may be used instead of, or in conjunction with, the palladium. Furthermore, one or more lanthanides other than, or in addition to, cerium may be used.

The examples above illustrate how cerium may be used as part of a support. Those skilled in the art will realise that cerium may be loaded onto a support which does not initially comprise cerium.

Whilst the present invention has been described and illustrated with reference to particular embodiments, it will be appreciated by those of ordinary skill in the art that the invention lends itself to many different variations not specifically illustrated herein. By way of example only, certain possible variations will now be described.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A method of producing at least one compound comprising an alkenyl group from at least one compound comprising an alkyl group having two or more carbon atoms, the method comprising:
   (i) Providing a mixture comprising carbon dioxide and at least one compound comprising an alkyl group having two or more carbon atoms, the mixture comprising at least 5 mol % carbon dioxide; and
   (ii) Contacting said mixture with a catalyst comprising (a) one or both of palladium and platinum, and (b) one or more of the lanthanide series of elements, thereby converting at least a portion of the at least one compound comprising an alkyl group having two or more carbon atoms into a compound comprising an alkenyl group, wherein the catalyst comprises at least 2.0 mol % and up to 15.0 mol % palladium, platinum or combination thereof based on a total for palladium and/or platinum relative to total catalyst,
   wherein a molar ratio of the one or more of the lanthanide series of elements to the one or both of palladium and platinum is from 1:1 to 15:1 in the catalyst, and
   wherein the contacting in step (ii) is conducted at a temperature of at least 300° C. and up to 600° C.

2. The method according to claim 1 in which the step (ii) takes place in the absence of steam, oxygen and/or hydrogen.

3. The method according to claim 1 in which the compound(s) comprising the alkyl group having two or more carbon atoms is a $C_2$-$C_2$ alkane or an alkyl aryl compound.

4. The method according to claim 1 in which the step (ii) is conducted at a temperature of at least 450° C. and up to 600° C.

5. The method according to claim 1 in which the mixture comprises from 25-40 mol % carbon dioxide.

6. The method according to claim 1 in which the mixture comprises from 25-40 mol % of the at least one compound comprising an alkyl group having two or more carbon atoms.

7. The method according to claim 1 in which a molar ratio of carbon dioxide to the at least one compound comprising an alkyl group having two or more carbon atoms is from 0.3:1 to 3:1.

8. The method according to claim 1 in which the mixture comprises up to 40 mol % of one or more inert component.

9. The method according to claim 1 further comprising a step of contacting at least a portion of the mixture with the catalyst more than once.

10. The method according to claim 1 further comprising passing a treated portion of the mixture from a position downstream of the catalyst to the catalyst.

11. The method according to claim 1 in which the catalyst comprises at least 2.0 mol % and up to 15.0 mol % of the one or more of the lanthanide series of elements.

12. The method according to claim 1 in which the one or more of the lanthanide series of elements is selected from the group consisting of lanthanum, cerium, praseodymium, neodymium, samarium, terbium, and combinations thereof.

13. The method according to claim 1 in which the one or more of the lanthanide series of elements is cerium.

14. The method according to claim 1 in which the catalyst further comprises a thermal stabiliser for stabilising the one or more of the lanthanide series of elements.

15. The method according to claim 14 in which the thermal stabiliser comprises zirconium.

16. The method according to claim 15 in which a molar ratio of the zirconium to the one or more of the lanthanide series of elements is at least 1:4 and no more than 2:1.

17. The method according to claim 15 in which the catalyst comprises at least 2.0 mol % zirconium, and up to 12.0 mol % zirconium.

18. The method according to claim 1 in which the catalyst comprises at least 4.0 mol % and up to 20.0 mol % aluminum.

19. The method according to claim 1 in which the catalyst comprises aluminum and in which a molar ratio of the aluminum to the one or more of the lanthanide series of elements is from 1:2 to 3:1.

20. The method according to claim 1 in which the catalyst comprises at least 1.0 mol % of the one or more of the lanthanide series of elements.

21. The method according to claim 1 in which the catalyst comprises at least 3.0 mol % and up to 15.0 mol % palladium, platinum or combination thereof based on a total for palladium and platinum relative to total catalyst.

* * * * *

UNITED STATES PATENT AND TRADEMARK OFFICE
CERTIFICATE OF CORRECTION

Page 1 of 1

PATENT NO. : 10,968,148 B2
APPLICATION NO. : 15/755157
DATED : April 6, 2021
INVENTOR(S) : Graham John Hutchings et al.

It is certified that error appears in the above-identified patent and that said Letters Patent is hereby corrected as shown below:

In the Specification
1. In Column 8, Line 44, delete "0," and insert -- O, --, therefor.

In the Claims
2. In Column 12, Line 8, in Claim 3, delete "C2-C2" and insert -- C2-C12 --, therefor.

Signed and Sealed this
Tenth Day of August, 2021

Drew Hirshfeld
*Performing the Functions and Duties of the
Under Secretary of Commerce for Intellectual Property and
Director of the United States Patent and Trademark Office*